United States Patent [19]

Yokomichi et al.

[11] 4,420,618

[45] Dec. 13, 1983

[54] PROCESS FOR PRODUCING 5-CHLORO-β-TRIFLUOROMETHYLPYRIDINES

[75] Inventors: Isao Yokomichi, Moriyama; Takahiro Haga, Kusatsu; Rikuo Nasu, Kyoto; Kuniaki Nagatani; Toshio Nakajima, both of Kusatsu, all of Japan

[73] Assignee: Ishihara Sangyo Kaisha Ltd., Osaka, Japan

[21] Appl. No.: 401,744

[22] Filed: Jul. 26, 1982

Related U.S. Application Data

[63] Continuation of Ser. No. 237,481, Feb. 23, 1981, abandoned.

[30] Foreign Application Priority Data

Mar. 7, 1980 [JP] Japan .................. 55-28826

[51] Int. Cl.³ .................. C07D 213/26; C07D 213/61
[52] U.S. Cl. .................. 546/345
[58] Field of Search .................. 546/345

[56] References Cited

U.S. PATENT DOCUMENTS

| | | | |
|---|---|---|---|
| 3,418,323 | 12/1968 | Johnston et al. | 546/345 |
| 3,538,100 | 11/1970 | Smith | 546/345 |
| 4,184,041 | 1/1980 | Nishiyama et al. | 546/345 |
| 4,227,001 | 10/1980 | Dietsche et al. | 546/345 |
| 4,257,857 | 3/1981 | Whittaker et al. | 546/345 |
| 4,288,600 | 9/1981 | Roberts et al. | 546/345 |
| 4,309,548 | 1/1982 | Wilson et al. | 546/345 |
| 4,331,811 | 5/1982 | Werner et al. | 546/345 |

FOREIGN PATENT DOCUMENTS

| | | | |
|---|---|---|---|
| 5064 | 10/1979 | European Pat. Off. | 546/345 |
| 1243196 | 6/1967 | Fed. Rep. of Germany . | |
| 55-2673 | 1/1980 | Japan . | |
| 55-147261 | 11/1980 | Japan . | |
| 2091718 | 8/1982 | United Kingdom | 546/345 |

OTHER PUBLICATIONS

PCT Patent Publication GB 78/00008.

*Primary Examiner*—Ethel G. Love
*Attorney, Agent, or Firm*—Oblon, Fisher, Spivak, McClelland & Maier

[57] ABSTRACT

5,6-Dichloro-β-trifluoromethylpyridine or 2,5,6-trichloro-β-trifluoromethylpyridine is produced by reacting 6-chloro-β-trifluoromethylpyridine or 2,6-dichloro-β-trifluoromethylpyridine with chlorine gas to chlorinate the 5-position of pyridine nucleus thereof:

(1) at a temperature of 100° C. to 250° C. and at least sufficient amount of chlorine for the reaction;
(2) in the presence of the catalyst of amount of at least 40% by weight (based on the 6-chloro or/and 2,6-dichloro-β-trifluoromethylpyridine), the catalyst being chlorides a metallic element selected from the group consisting of iron, tungsten, molybdenum, titanium, and antimony.

9 Claims, No Drawings

4,420,618

PROCESS FOR PRODUCING 5-CHLORO-β-TRIFLUOROMETHYLPYRIDINES

This is a continuation of application Ser. No. 237,481, filed Feb. 23, 1981, now abandoned.

BACKGROUND OF THE INVENTION

1. Field of the Invention

The present invention relates to a process for chlorinating the 5-position of pyridine nucleus of β-trifluoromethylpyridines with chlorine gas in the presence of a specific catalyst.

2. Description of the Prior Art

Recently, 5-chloro-β-trifluoromethylpyridines having trifluoromethyl group at β-position of the pyridine nucleus and chlorine atom at 5-position thereof have been considered to be remarkably useful as intermediates for medicines and agricultural chemicals such as herbicides, fungicides and insecticides.

5-Chloro-β-trifluoromethylpyridines include 5,6-dichloro or 2,5,6-trichloro-β-trifluoromethylpyridine. These compounds will be referred to as 5-chloro-β-trifluoromethylpyridines.

It has been difficult to produce 5-chloro-β-trifluoromethylpyridines in an industrial process. For example, the process for producing 5,6-dihalogeno-β-trifluoromethylpyridine has been disclosed in WO 79/00094. The process is a small laboratory scale process and is not suitable as an industrial process. In this process, 6-amino-β-methylpyridine is brominated to produce 6-amino-5-bromo-β-methylpyridine and the product is diazotizated and chlorinated followed by chlorinating it under UV irradiation to produce 5,6-dichloro-β-trichloromethylpyridine, and the product is further fluorinated with antimony fluoride to produce 5,6-dichloro-β-trifluoromethylpyridine. The starting material in the process is, however, remarkably expensive and the operation is complicated in many reaction steps to be disadvantageous as an industrial process.

It has been succeeded in the industrial production of β-trifluoromethylpyridines such as 6-chloro, or 2,6-dichloro-β-trifluoromethylpyridine from β-picoline and accordingly it has been studied to produce 5-chloro-β-trifluoromethylpyridines from β-trifluoromethylpyridines. Hereinafter, 6-chloro or 2,6-dichloro-β-trifluoromethylpyridine will be referred to as β-trifluoromethylpyridines. In the study, 6-chloro-β-trifluoromethylpyridine is treated with ammonia water under an elevated pressure to produce 6-amino-β-trifluoromethylpyridine and the product is chlorinated to produce 6-amino-5-chloro-β-trifluoromethylpyridine and the product is diazotizated and chlorinated to produce 5,6-dichloro-β-trifluoromethylpyridine. In this process, however, the reaction should be disadvantageous carried out under an elevated pressure in many reaction steps and moreover, the treatment of wasted water is not easy.

SUMMARY OF THE INVENTION

It has been found that 5-chloro-β-trifluoromethylpyridines as the object compound have been produced by chlorinating the β-trifluoromethylpyridines with chlorine gas in the presence of a specific catalyst without any trouble.

It is an object of the present invention to provide a process for producing 5-chloro-β-trifluoromethylpyridines.

It is another object of the present invention to provide a process for producing the object compound with industrial advantages of mild reaction condition in less side-reaction and less reaction steps.

It is the other object of the present invention to provide a process for producing the object compound in high yield with an economical, easily commercially available starting material and a catalyst.

The other objects of the present invention will be clear by the following description.

The foregoing and other objects of the present invention have been attained by providing a process for producing 5,6-dichloro-β-trifluoromethylpyridine or 2,5,6-trichloro-β-trifluoromethylpyridine which comprises reacting 6-chloro-β-trifluoromethylpyridine or 2,6-dichloro-β-trifluoromethylpyridine with chlorine gas to chlorinate the 5-position of pyridine nucleus thereof:

(1) at a temperature of 100° C. to 250° C. and at least sufficient amount of chlorine for the reaction;

(2) in the presence of the catalyst of amount of at least 40% by weight (based on the 6-chloro or/and 2,6-dichloro-β-trifluoromethylpyridine), the catalyst being chlorides of metallic element selected from the group consisting of iron, tungsten, molybdenum, titanium, and antimony.

DETAILED DESCRIPTION OF THE PREFERRED EMBODIMENTS

The β-trifluoromethylpyridines such as 6-chloro-β-trifluoromethylpyridine and 2,6-dichloro-β-trifluoromethylpyridine used as the starting materials in the present invention can be easily produced by reacting β-picoline with chlorine gas and hydrogen fluoride in the presence of a specific metal fluoride at 350° to 450° C. in a vapor phase. The process is disclosed in Japanese Unexamined Patent Publication No. 147261/1980.

The specific metal chlorides used as the catalyst in the present invention can be ferric chloride, tungsten hexachloride, molybdenum pentachloride, titanium tetrachloride, and antimony pentachloride. Certain metal chloride can be formed in the reaction system as the desired metal chloride by reacting a metal powder with chlorine gas by adding the metal powder in the reaction system. The optimum catalyst among the metal chlorides are iron chlorides and antimony chlorides, especially ferric chloride. It is possible to incorporate a small amount of iodine as a cocatalyst.

An amount of the catalyst is not critical and is preferably at least 40 wt.%, preferably 40 to 200 wt.% especially 60 to 150 wt.% based on the β-trifluoromethylpyridines as the starting material. When the amount of the catalyst is less than 40 wt.% based on the β-trifluoromethylpyridines, the desired chlorination can not be performed or can be delayed.

In general, the β-trifluoromethylpyridines as the starting material and chlorine gas are heated at higher than 100° C. preferably 100° to 250° C. in the presence of the catalyst in the process of the present invention. The reaction can be carried out under the atmospheric pressure or the elevated pressure.

An amount of chlorine gas is not critical and is large enough to perform the chlorination and is usually in a range of 1 to 20 mole preferably 1 to 10 mole per 1 mole of β-trifluoromethylpyridines.

In the reaction of the present invention, 5-position of pyridine nucleus of the β-trifluoromethylpyridines as the starting material is selectively chlorinated to produce advantageously 5-chloro-β-trifluoromethylpyridines as the object product. The reaction is usually completed for 1 to 40 hours.

The separation of the object product from the reaction mixture can be easily attained by the conventional purification and separation methods such as an extraction, a washing and a distillation. The object product can be obtained in high yield such as higher than 70% based on the exhausted β-trifluoromethylpyridines as the starting material.

The present invention will be further illustrated by certain examples and references which are provided for purposes of illustration only and are not intended to be limiting the present invention.

EXAMPLE 1

In a 1 liter four necked flask equipped with a thermometer, a refluxing condenser and a chlorine gas inlet pipe, 363 g. of 6-chloro-β-trifluoromethylpyridine and 325 g. of ferric chloride were charged and chlorine gas was fed under refluxing the mixture by heating to react them at 150° to 170° C. for 18 hours. The reaction mixture was poured into 1.5 liter of hot water to separate 340 g. of an oily product. The oily product was dehydrated over anhydrous sodium sulfate and then, was distilled to obtain 163 g. of 5,6-dichloro-β-trifluoromethylpyridine.

EXAMPLE 2

In a 50 ml. autoclave, 9.1 g of 6-chloro-β-trifluoromethylpyridine and 8.1 g. of ferric chloride were charged and 0.15 mole of chlorine gas was fed to react them at 190° C. for 5 hours under an elevated pressure. In accordance with the process of Example 1, the reaction mixture was purified to obtain 7.6 g. of 5,6-dichloro-β-trifluoromethylpyridine.

EXAMPLE 3

In a 50 ml. four necked flask equipped with a thermometer, a refluxing condenser and a chlorine gas inlet pipe, 30 g. of 6-chloro-β-trifluoromethylpyridine and 15.0 g. of tungsten hexachloride were charged and chlorine gas was fed with stirring the mixture to react them at 140° to 150° C. for 15 hours. The reaction product was extracted with 200 ml. of methylene chloride and the solvent layer was washed twice with water and dehydrated over anhydrous sodium sulfate and then the solvent was distilled off and the product was distilled at 97° to 99° C. under a pressure of 86 mmHg. to obtain 10.1 g of 5,6-dichloro-β-trifluoromethylpyridine.

EXAMPLES 4 TO 6

In accordance with the process of Example 3, except using 18 g. of each catalyst shown in Table 1 instead of 15.0 g. of tungsten hexachloride, each reaction was carried out and the product was purified to obtain 5,6-dichloro-β-trifluoromethylpyridine as the object compound. The results are shown in Table 1.

TABLE 1

| Example | Catalyst | Yield of object compound (g) |
| --- | --- | --- |
| 4 | TiCl4 | 13.3 |
| 5 | SbCl5 | 16.2 |
| 6 | MoCl5 | 12.5 |

EXAMPLE 7

In a 200 ml. four necked flask equipped with a thermometer, a refluxing condenser and a chlorine gas inlet pipe, 108 g. of 2,6-dichloro-β-trifluoromethylpyridine and 81 g. of ferric chloride were charged and chlorine gas was fed to react them by heating at 170° to 210° C. for 17 hours. The reaction mixture was poured into 0.4 liter of hot water to separate an oily product. The oily product was dehydrated over anhydrous sodium sulfate and the product was distilled and further rectified to obtain 30 g. of 2,5,6-trichloro-β-trifluoromethylpyridine.

EXAMPLE 8

In the same flask used in Example 7, 45.4 g. of 6-chloro-β-trifluoromethylpyridine and 13.6 g. of iron powder were charged and chlorine gas was fed to react them at 150° to 170° C. The reaction was performed for 17 hours in the presence of ferric chloride formed by chlorination of the iron powder. The reaction mixture was poured in 0.2 liter of hot water. In accordance with the process of Example 7, the product was purified to obtain 9 g. of 5,6-dichloro-β-trifluoromethylpyridine.

EXAMPLE 9

In a 300 ml. four necked flask equipped with a thermometer, a refluxing condenser and a chlorine gas inlet pipe, 100 g. of 6-chloro-β-trifluoromethylpyridine, 84.6 g. of ferric chloride and 8.2 g. of antimony pentachloride were charged and chlorine gas was fed under refluxing the mixture by heating to react them at 140° to 160° C. for 10 hours. The reaction mixture was poured into 300 ml. of water to separate 95 g. of an oily product. The oily product was dehydrated over anhydrous sodium sulfate and was rectified to obtain 48 g. of 5,6-dichloro-β-trifluoromethylpyridine.

EXAMPLE 10

In accordance with the process of Example 9, except using 72.9 g. of ferric chloride, 14.9 g. of antimony pentachloride and 13.6 g. of molybdenum pentachloride instead of 84.6 g. of ferric chloride and 8.2 g. of antimony pentachloride, the reaction and the purification were carried out to obtain 43 g. of 5,6-dichloro-β-trifluoromethylpyridine.

EXAMPLE 11

In accordance with the process of Example 9 except using 72.9 g. of ferric chloride, 14.9 g. of antimony pentachloride, 13.6 g. of molybdenum pentachloride and 9.5 g. of titanium tetrachloride instead of 84.6 g. of ferric chloride and 8.2 g. of antimony pentachloride, the reaction and the purification were carried out to obtain 40 g. of 5,6-dichloro-β-trifluoromethylpyridine.

We claim:

1. A process for producing 5,6-dichloro-β-trifluoromethylpyridine or 2,5,6-trichloro-β-trifluoromethylpyridine which comprises reacting 6-chloro-β-trifluoromethylpyridine or 2,6-dichloro-β-trifluoromethylpyridine with chlorine gas to chlorinate the 5-position of the pyridine nucleus thereof:
   (1) at a temperature of 100° C. to 250° C. and at least sufficient amount of chlorine for the reaction;
   (2) in the presence of a catalyst of amount of at least 40% by weight (based on the 6-chloro or/and 2,6-dichloro-β-trifluoromethylpyridine), the catalyst being chlorides of a metallic element selected from the group consisting of iron, tungsten, molybdenum, titanium, and antimony.

2. A process according to claim 1 wherein said amount of catalyst is in a range of 40% to 200% by weight based on the 6-chloro or/and 2,6-dichloro-β-trifluoromethylpyridine.

3. A process for producing 5,6-dichloro-β-trifluoromethylpyridine according to claim 1 which comprises reacting 6-chloro-β-trifluoromethylpyridine with chlorine gas.

4. A process according to claim 3 wherein the reaction is carried out at a temperature of 100° C. to 250° C. in the presence of the catalyst of amount of at least 40% by weight based on said 6-chloro-β-trifluoromethylpyridine.

5. A process according to claim 3 wherein the reaction is carried out at a temperature of 100° C. to 250° C., and in the presence of ferric chloride or antimony pentachloride as the catalyst at an amount of 40% to 200% by weight based on said 6-chloro-β-trifluoromethylpyridine.

6. A process according to claim 3 wherein the catalyst is ferric chloride.

7. A process for producing 2,5,6-trichloro-β-trifluoromethylpyridine according to claim 1 which comprises reacting 2,6-dichloro-β-trifluoromethylpyridine with chlorine gas.

8. A process according to claim 7 wherein the reaction is carried out at a temperature of 100° C. to 250° C. in the presence of the catalyst of amount of at least 40% by weight based on said 2,6-dichloro-β-trifluoromethylpyridine.

9. A process according to claim 7 wherein the reaction is carried out at a temperature of 100° C. to 250° C., and in the presence of ferric chloride or antimony pentachloride as the catalyst at an amount of 40% to 200% by weight based on said 2,6-dichloro-β-trifluoromethylpyridine.

* * * * *